(12) United States Patent
Bansbach et al.

(10) Patent No.: US 11,389,083 B2
(45) Date of Patent: Jul. 19, 2022

(54) METHOD, DEVICE AND SYSTEM FOR SENSING NEUROMUSCULAR, PHYSIOLOGICAL, BIOMECHANICAL, AND MUSCULOSKELETAL ACTIVITY

(71) Applicant: University of Pittsburgh—Of the Commonwealth System of Higher Education, Pittsburgh, PA (US)

(72) Inventors: Heather Bansbach, Chesterfield, VA (US); Timothy Crawford Sell, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 362 days.

(21) Appl. No.: 15/766,165

(22) PCT Filed: Oct. 6, 2016

(86) PCT No.: PCT/US2016/055635
§ 371 (c)(1),
(2) Date: Apr. 5, 2018

(87) PCT Pub. No.: WO2017/062544
PCT Pub. Date: Apr. 13, 2017

(65) Prior Publication Data
US 2018/0279919 A1    Oct. 4, 2018

Related U.S. Application Data

(60) Provisional application No. 62/237,666, filed on Oct. 6, 2015.

(51) Int. Cl.
*A61B 5/11* (2006.01)
*A61B 5/00* (2006.01)
*A61B 5/22* (2006.01)

(52) U.S. Cl.
CPC .......... *A61B 5/1118* (2013.01); *A61B 5/1121* (2013.01); *A61B 5/22* (2013.01);
(Continued)

(58) Field of Classification Search
CPC ....... A61B 5/1118; A61B 5/1121; A61B 5/22; A61B 5/45; A61B 2562/0219
See application file for complete search history.

(56) References Cited

U.S. PATENT DOCUMENTS 8,107,920 B2    1/2012   Ben Ayed
8,964,298 B2    2/2015   Haddick et al.
(Continued)

FOREIGN PATENT DOCUMENTS

WO    2012025622 A2    3/2012

OTHER PUBLICATIONS

Heebner et al., "Reliability and validity of an accelerometry based measure of static and dynamic postural stability in healthy and active individuals", Gait & Posture, 2014, vol. 41 issue 2, pp. 535-539.
(Continued)

*Primary Examiner* — Daniel L Cerioni
*Assistant Examiner* — Raymond P Dulman
(74) *Attorney, Agent, or Firm* — The Webb Law Firm

(57) ABSTRACT

A neuromuscular, physiological, biomechanical, or musculoskeletal activity monitoring system for a subject is provided. The system includes a wearable inertial measurement unit including at least one accelerometer and/or at least one gyroscope. The system also includes a controller in communication with an output component. The controller is configured to: receive and process information from the inertial measurement unit representative of one or more physical actions performed by the subject; generate an inertial data set for the one or more physical actions based
(Continued)

on the received and processed information; compare the generated inertial data set to reference data stored on computer readable memory in communication with the controller; and cause the output component to provide feedback including predictive injury information. The predictive injury information is based, at least in part, on the comparison between the generated data set and the reference data.

14 Claims, 9 Drawing Sheets

(52) U.S. Cl.
CPC ............. *A61B 5/45* (2013.01); *A61B 5/486* (2013.01); *A61B 5/6801* (2013.01); *A61B 5/743* (2013.01); *A61B 5/744* (2013.01); *A61B 5/7435* (2013.01); *A61B 2503/10* (2013.01); *A61B 2505/09* (2013.01); *A61B 2560/0223* (2013.01); *A61B 2560/0462* (2013.01); *A61B 2562/028* (2013.01); *A61B 2562/0219* (2013.01); *A61B 2562/0247* (2013.01); *A63B 2220/00* (2013.01)

(56) References Cited

U.S. PATENT DOCUMENTS

| | | |
|---|---|---|
| 9,161,705 B2 | 10/2015 | Tamil et al. |
| 9,168,419 B2 | 10/2015 | Hong et al. |
| 2012/0179055 A1 | 7/2012 | Tamil et al. |
| 2012/0268592 A1* | 10/2012 | Aragones ............ A61B 5/6807 348/143 |
| 2013/0127980 A1 | 5/2013 | Haddick et al. |
| 2013/0171599 A1* | 7/2013 | Bleich .................. A63B 15/00 434/247 |
| 2013/0217352 A1* | 8/2013 | Pan ..................... A61B 5/1112 455/404.1 |
| 2013/0253375 A1* | 9/2013 | Dreifus ............... A61B 5/4538 600/587 |
| 2014/0149067 A1* | 5/2014 | Merril ................... A61B 5/11 702/141 |
| 2014/0159894 A1 | 6/2014 | Tropper et al. |
| 2014/0228985 A1* | 8/2014 | Elliott ............... G06F 19/3481 700/91 |
| 2014/0276242 A1 | 9/2014 | Chen et al. |
| 2014/0278229 A1 | 9/2014 | Hong et al. |
| 2015/0134268 A1 | 5/2015 | Yuen et al. |
| 2015/0186613 A1 | 7/2015 | Park et al. |
| 2015/0257682 A1* | 9/2015 | Hansen ............. A41D 19/0027 382/103 |
| 2016/0015972 A1* | 1/2016 | Hyde .................. A61B 5/0022 607/48 |
| 2016/0263439 A1* | 9/2016 | Ackland ............. A61B 5/4836 |
| 2017/0265784 A1* | 9/2017 | Santello ................ A61B 5/11 |

OTHER PUBLICATIONS

Sell et al., "Relationship between tibial acceleration and proximal anterior tibia shear force across increasing jump distance", Journal of Applied Biomechanics, 2014, vol. 30, pp. 75-81.

* cited by examiner

METHOD, DEVICE AND SYSTEM FOR SENSING NEUROMUSCULAR, PHYSIOLOGICAL, BIOMECHANICAL, AND MUSCULOSKELETAL ACTIVITY

CROSS-REFERENCE TO RELATED APPLICATIONS

This application is the United States national phase of international Application No. PCT/US2016/055635 filed Oct. 6, 2016, and claims the benefit of U.S. Provisional Patent Application Ser. No. 62/237,666, filed Oct. 6, 2015, each of which is hereby incorporated by reference in its entirety.

STATEMENT REGARDING FEDERALLY SPONSORED RESEARCH

This invention was made with government support under Grant No. 1449702 awarded by the National Science Foundation. The government has certain rights in the invention.

BACKGROUND

Technical Field

The present disclosure relates to devices, systems, and methods for sensing neuromuscular, physiological, biomechanical, and musculoskeletal activity of an individual and, in some instances, to providing feedback related to injury prediction based on sensed information.

Background

More than 65 million Americans annually suffer from a musculoskeletal injury, costing approximately 900 billion dollars each year. Musculoskeletal injuries include injury to the muscles, nerves, tendons, or joints. A majority of these injuries are preventable. Current efforts for injury prevention include obtaining measures of neuromuscular, physiological, biomechanical, and musculoskeletal characteristics at specialized labs. Data is collected and interpreted by clinicians. For example, movement assessment labs may be set up at training facilities for elite athletes or military personnel. However, such specialized laboratory equipment, while reliable and valid, is expensive and requires trained personnel for both data collection (e.g., instructing the subject to perform activities and exercises) and for analysis of collected data. In addition, costs and time associated with traveling to a specialized laboratory limits a large portion of the population from accessing these services.

Numerous wearable fitness monitoring devices are available for use by laypersons, such as recreationally and/or occupationally active individuals. These devices often include movement sensors for identifying motion of a subject wearing the device. For example, such devices can measure and provide feedback for parameters including steps taken, distance traveled, speed, time in motion or exercise duration, as well as calories burned and other health related parameters. Exemplary fitness monitoring devices are disclosed in U.S. Pat. No. 9,168,419 and in U.S. Patent Appl. Pub. Nos. 2014/0159894 and 2015/0134268, each of which is incorporated by reference in its entirety to the extent of its technical disclosure and only in a manner consistent with the present disclosure. However, such fitness monitoring devices do not provide sufficiently detailed measurements for movement analysis and do not provide predictive feedback related to injury risks.

SUMMARY

The devices, systems, and methods described herein are configured for collecting valid and reliable data outside of a laboratory environment and, often, without input from trained clinicians or physical therapists. As such, these devices, systems, and methods are capable of providing more sophisticated analysis and feedback concerning movement of a subject than is provided using conventional fitness monitor devices. In one example, the collected data is used for providing predictive feedback related to injury risk and recommended training regimens based on collected movement information. As such, these devices and systems are capable of providing automated feedback related to subject movement, which previously was only available from clinical analysis of movement data collected at specialized laboratory locations. As a result, these devices, systems, and methods provide non-invasive and inexpensive evaluation of movement and musculoskeletal loading which can be made available to a wide variety of participants and subjects.

In accordance with an aspect of the disclosure, a neuromuscular, physiological, biomechanical, or musculoskeletal activity monitoring system for a subject is provided. The system comprises a wearable inertial measurement unit comprising at least one accelerometer and/or at least one gyroscope. The inertial measurement unit is configured to be worn by the subject. The system also comprises a controller in communication with an output component. The controller is configured to: receive and process information from the inertial measurement unit representative of one or more physical actions performed by the subject; generate an inertial data set for the one or more physical actions based on the received and processed information; compare the generated inertial data set to reference data stored on computer readable memory in communication with the controller; and cause the output component to provide feedback comprising predictive injury information. The predictive injury information is based, at least in part, on the comparison between the generated data set and the reference data.

In another aspect, a method of monitoring neuromuscular, physiological, biomechanical, or musculoskeletal activity of a subject is provided. The method comprises: placing an inertial measurement unit comprising at least one accelerometer and/or at least one gyroscope on the subject; obtaining information representative of one or more inertial data sets from the inertial measurement unit during one or more physical actions performed by the subject; comparing the generated one or more inertial data sets to reference data for the one or more physical actions; and determining predictive injury information for the one or more physical actions performed by the subject, the predictive injury information being based, at least in part, on the comparison between the generated inertial data set and the reference data.

In another aspect, a computer implemented method for monitoring neuromuscular, physiological, biomechanical, or musculoskeletal activity of a subject based on information received from a wearable inertia measurement unit and adapted to be performed on a portable computing device is provided. The computer-implemented method comprises: receiving and processing information from the inertial measurement unit representative of one or more physical actions performed by the subject; generating an inertial data set for the one or more physical action based on the received and processed information; comparing the generated inertial data set to reference data stored on computer readable memory in communication with the portable computing device; and causing an output component of the portable computing device to provide feedback comprising predictive injury information, the predictive injury information being based, at least in part, on the comparison between the generated inertial data set and the one or more reference data sets.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION OF THE INVENTION

Figure 1A:
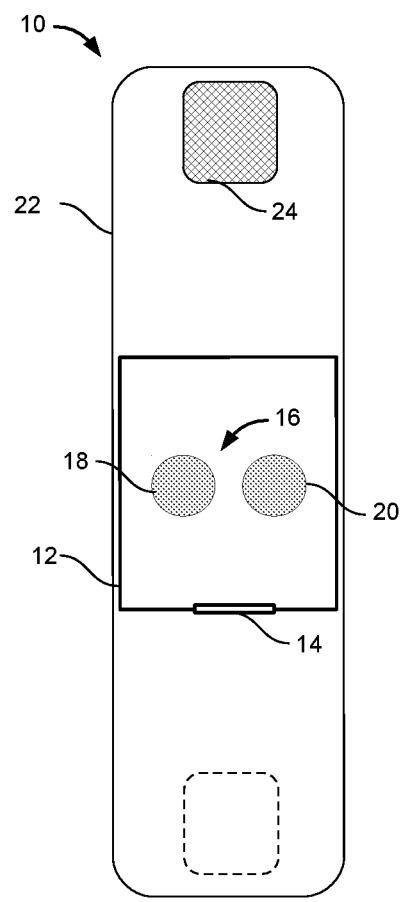
FIG. 1A is a schematic drawing of an exemplary wearable sensor device including an inertial measurement unit according to an aspect of the disclosure.

As used herein, the singular form of "a", "an", and "the" include plural references unless the context clearly dictates otherwise.

As used herein, the terms "right", "left", "top", "bottom", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless indicated to the contrary, the numerical parameters set forth in the following specification and attached claims are approximations that can vary depending upon the desired properties sought to be obtained by the present disclosure.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are also possible.

According to an aspect of the disclosure, a wearable sensor device for obtaining information about movement of a subject, such as a patient, athlete, or animal, performing certain actions and activities is provided. In some examples, an action or activity is a motion performed or attempted by the subject, such as moving a body portion or performing an exercise, such as running, jumping, turning, throwing, twisting, or virtually any motion a subject is capable of performing or attempting to perform. In some examples, the wearable sensor device is a wearable biometric device configured to obtain acceleration, positioning, and/or angular motion data for the subject. For example, the wearable sensor device can include commercially available motion and movement sensors, such as an inertial measurement unit.

An inertial measurement unit is an electronic device that measures and reports movement and positioning data (e.g., an inertial data set) including specific force, velocity, acceleration, and angular rate using a combination of accelerometers and gyroscopes. Inertial measurement units are commonly used in inertial navigation systems for aircrafts. When used in an aircraft, an inertial measurement unit is used for detecting a current rate of acceleration in multiple axis (e.g., acceleration in the x, y, and z directions) with one or more linear accelerometers, and for detecting rotational attributes like pitch, roll, and yaw using one or more or angular accelerometers and/or gyroscopes. Measurements from the accelerometers and gyroscopes can also be used for calculating changes in position of the device. In one example, a commonly used inertial measurement unit design includes three accelerometers positioned to measure acceleration along three axes which are orthogonal to one another (e.g., the x, y, and z axes). The inertial measurement unit also includes three gyroscopes placed in a similar orthogonal pattern for measuring rotational position of the sensor device around each of the axes. Information from the six sensors can be combined together using different positioning algorithms to determine an absolute or relative position of the wearable sensor device.

While acceleration and angular momentum information can also be collected from multipurpose electronic devices, such as smart phones, which use the innate mobile device accelerometer technology to obtain an angular motion data, such smartphone devices are not meant to be worn on the person's extremity and therefore require assistance of an additional person to collect movement data. In addition, data received from accelerometers on smart phone devices generally do not have the requisite level of accuracy provided by the wearable sensor devices disclosed herein. For example, the innate accelerometer technologies used by smartphone devices may not have an appropriate range or specificity to measure data for some assessments, such as dynamic balance. Dynamic balance has been determined to be a more appropriate measure of balance in healthy, active populations, than static balance. As will be appreciated by one of ordinary skill in the art, accuracy and precision of the assessments are needed to identify risk of injury appropriately from measured movement data.

The wearable device desirably is sufficiently lightweight and flexible to be worn on the subject's extremity and not to interfere with the subject's normal range of motion. In some instances, the wearable sensor device allows the subject to self-administer physiological biomechanical and/or musculoskeletal assessments and to receive predictive results without needing input and/or analysis of collected data by a clinician. Advantageously, multiple assessments can be performed using the same wearable sensor device. For example, the wearable sensor device can be placed on different extremities or positions for different types of assessments. Results from different assessments can be considered together to provide a more comprehensive indication of patient physical fitness, strength, or injury risk. Another advantage is that assessments based on information measured by the biometric wearable sensor device can be performed at any location, meaning that individuals do not need to travel to a specialized lab or clinic to perform physiological assessment activities.

In some instances, the biometric wearable sensor device wirelessly communicates with a nearby computing or communication device (referred to herein as an intermediary device), such as a portable computing device, cellular telephone, smart phone, or Internet gateway device, to drive data collection and analysis. In some examples, the intermediary device comprises a controller configured to implement software for receiving and processing information from the wearable sensor device and for providing feedback to a user based on the movement information. In some examples, feedback includes identifying individuals who are at risk for injury based on measurable characteristics of the subject's fitness level, body type, strength, flexibility and other characteristics. Feedback can also include recommendations for training regimens for the subject based on measured information. In some instances, results from different assessments can be considered together to determine personalized training recommendations. For example, a personalized training recommendation for a recreationally active individual with low flexibility and low postural strength includes performing exercise for strengthening or improving flexibility of certain identified muscle groups. The training recommendations can also include other exercises or activities related to certain neuromuscular, physiological, biomechanical, and musculoskeletal characteristics and deficiencies. The training recommendations can decrease injury risk, enhance rehabilitation efforts, and improve athletic performance. Desirably, by adopting and adhering to the training recommendations, subjects can avoid invasive medical procedures, as well as missed work days and missed active days.

According to another aspect of the disclosure, acquisition and storage of data is performed on a regular basis. For example, measured results can be stored in a database of inertial data sets either automatically or manually at the request of a user or system administrator. In some instances, measurement is performed on the subject two or more times, such as during an initial patient evaluation and after the treatment regimen has been followed for a few days or weeks. A data set acquired at the earlier or initial time point can be compared to a data set acquired at the later time. The deviation between the data sets at different time points can be analyzed either automatically by a computing device (e.g., the intermediary device), or by a user, technician or administrator, to decide whether actions or activities recommended by system (e.g., the recommended treatment regimen) achieve a desired outcome, such as improvement in strength, motion, and endurance. Results of the analysis are used to improve future treatment recommendations either for a particular subject or for all subjects using the devices and systems described herein.

Wearable Sensor Device

Figure 1B:
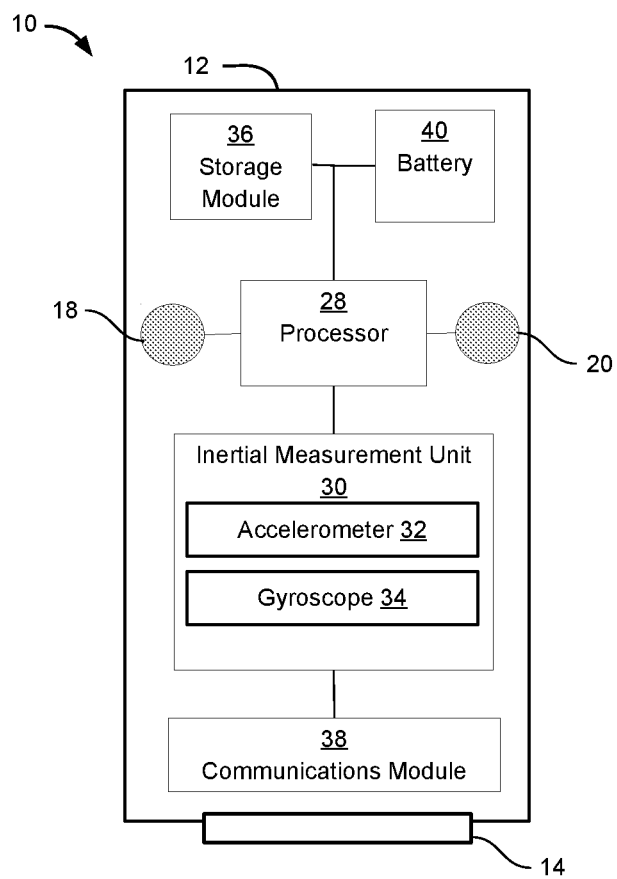
FIG. 1B is a schematic drawing of internal circuitry of the exemplary wearable sensor device of FIG. 1A.

FIGS. 1A and 1B show an exemplary wearable sensor device 10 for collecting movement information for a subject. In some examples, the device includes a housing 12 enclosing circuitry for collecting movement information. The housing 12 can be formed from a lightweight, rigid material such as plastic or brushed aluminum. In some instances, the housing 12 can include various removable covers or other openings for accessing interior components of the device 10, such as batteries, sensors, memory cards, and other items. The housing 12 can also include one or more ports 14, such as a USB or Firewire port, for wired connection between the wearable sensor device 10 and other computing devices. In some instances, the device 10 can include one or more visual indicators 16, such as LEDs, extending through the housing 12 for conveying information to a user. For example, a green-color LED 18 can be turned on when the device is ready to use. A red or yellow colored LED 20 can be turned on to indicate to the user that the device 10 is not ready to collect data if, for example, the device battery is depleted or if the device 10 does not include sufficient memory to record assessment measurements. In some instances, a visual indicator 16 can also be used to indicate when the device 10 is in wireless communication with another computer device and/or when the device 10 is uploading data to another computer device.

In some examples, the wearable sensor device 10 includes a harness, band, adhesive patch, or another connection mechanism for affixing or mounting the wearable sensor device 10 to the subject. For example, the wearable sensor device 10 may be mounted to a hand, wrist, arm, waist, leg, or ankle of the subject. In one aspect, as shown in FIG. 1A, the device 10 includes a strap 22 for attaching the device 10 to the user's waist. The strap 22 includes a connector 24, such as a buckle or hook and loop fastener (e.g., Velcro™), for attaching ends of the strap 22 together to hold it in place around the subject's wrist. In other examples, the device 10 can be attached to a necklace or collar and worn around the subject's neck. In still other examples, the device 10 can be affixed to the individual's clothing using a clip, clasp, or similar fastener.

With specific reference to FIG. 1B, internal circuitry of a wearable sensor device 10 is illustrated. As shown in FIG. 1B, the wearable sensor device 10 includes electronic circuitry, such as an inertial measurement unit 30, enclosed within the housing 12 for measuring movement information of the subject wearing the device 10. The device 10 also includes a storage module 36 comprising transitory or non-transitory computer readable memory for storing information collected by the inertial measurement unit 30.

The inertial measurement unit 30 comprises movement sensors, such as one or more single axis or multi-axis accelerometer(s) 32 and one or more gyroscope(s) 34. In some examples, the inertial measurement unit 30 includes three orthogonally positioned accelerometers and gyroscopes. An accelerometer measures acceleration. Most accelerometers can also measure tilt. The accelerometer was originally a large device, but with the continued advances in the field of micro-electromechanical systems (MEMS) technology, accelerometers are presently available in sizes of less than 1 or 2 mm, with 3-axis measurements. A gyroscope measures orientation. In one embodiment of the device 10, a gyroscope is used to determine changes in the orientation of the subjects' body to help identify the physical activity being performed. Gyroscopes based on MEMS technology are now also widely commercially available. Commercial chips that combine a 3-axis accelerometer and a 3-axis gyroscope are commercially available. One non-limiting example of a useful device is the WAX9 inertial measurement unit (IMU), commercially available from Axivity Ltd. of York, UK, having accelerometer and gyro functionality as well as Bluetooth connectivity, a magnetometer, a barometric sensor, a temperature sensor, a micro-USB connector, suitable firmware, and a processor.

In some examples, the wearable sensor device 10 also includes a timer 36 or clock. The timer 36 is used to record a time when certain data is collected. The acquisition time can be stored by the storage module 36 along with the collected data for providing a time-stamped record of physical activities performed by the subject.

As shown in FIG. 1B, the wearable sensor device 10 also includes a communications module 38 for wired or wireless communication with an external computing device. In some examples, the communications module 38 transmits collected data from the device 10 to another computer device automatically substantially in real time. In other examples, sensed information is collected and stored in the storage module 36 and uploaded to the computer device as a batch file transfer. Uploads can occur periodically according to a predetermined schedule or, for example, in response to an event, such as a request from the external computer device or when the wearable sensor device 10 is in proximity (e.g., within range for file transfer via short-range wireless data transmission) to the computer device. In some examples, the communications module 38 is a wireless transceiver, such as a transceiver employing IEEE 802 wireless networking standards, by Bluetooth®, Wi-Fi, ZigBee, LAN, WAN, cellular, connection, connections or combinations thereof. Wired data transmission may occur via USB, Firewire, or Ethernet networking standards.

In some examples, the wearable sensor device also includes power management components, such as a rechargeable battery 40 and associated control circuitry. For example, the control circuitry can monitor battery parameters such as charge remaining. In some examples, the device 10 provides output to a user when the battery 40 needs to be recharged or when the battery 40 is too depleted to continue data collection.

Movement Analysis System

Figure 2:
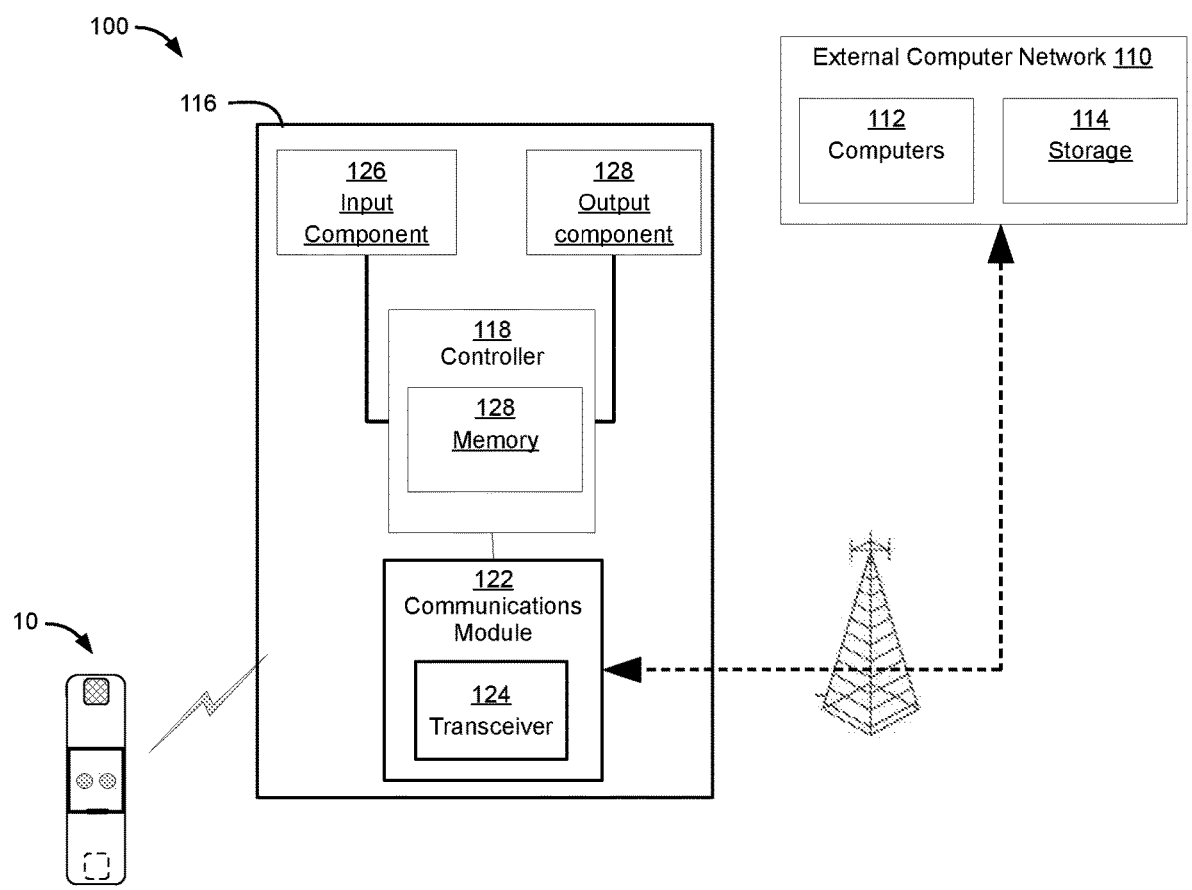
FIG. 2 is a schematic drawing of a movement analysis system including the wearable sensor device of FIG. 1A.

A movement analysis system 100 including one or more wearable sensor devices 10 is shown in FIG. 2. The movement analysis system 100 can be configured to obtain data from the wearable sensor device(s) 10 for the purpose of sensing and analyzing neuromuscular, physiological, biomechanical, and/or musculoskeletal activity of one or more subjects. The system 100 can include multiple wearable sensor devices 10 associated with one or more subjects. For example, wearable sensor devices 10 could be placed on different portions of a subject's body (e.g., a wearable sensor device worn around the wrist and another wearable sensor device worn around the waist) to simultaneously sense movement of different portions of the subject's body. In other examples, the system 100 includes wearable sensor devices 10 worn by multiple subjects. Data for the multiple subjects can be transmitted either directly or indirectly to a central device or server. For example, as shown in FIG. 2, the data is received by an external computer network 110 comprising one or more computing devices 112 in communication with storage devices 114 comprising computer readable memory comprising databases of movement results for various subjects.

Intermediary Device

In some examples, data from the wearable sensor device(s) 10 is first transmitted to an intermediary device 116, which receives data from the one or more wearable sensor devices 10 and transmits the data to the computer network 110. The intermediary device 116 can be a dedicated electronic device comprising non-transitory computer readable memory with instructions for receiving, processing, communicating/transmitting, and, in some cases, providing feedback about the information from the one or more wearable sensor devices 10.

In other examples, the intermediary device 116 is a multipurpose electronic or computer device capable of performing processes for data collection and analysis. In the context of computing, a process is, broadly speaking any computer-implemented activity that generates an outcome, such as implementation of a mathematical or logical formula, operation, or algorithm. For example, the intermediary device 116 can be a portable computer device, laptop computer, tablet, or smartphone (such as an Apple iPhone or a Samsung Galaxy). Other examples include a workstation, a server, a tablet, a smart device, a web-enabled telephone, a web-enabled personal digital assistant (PDA), a microprocessor, an integrated circuit, an application-specific integrated circuit, a microprocessor, a microcontroller, a network server, a Java™ virtual machine, a logic array, a programmable logic array, a micro-computer, a mini-computer, a large frame computer, or any other component, machine, tool, equipment, or some combination thereof capable of responding to and executing instructions. The portable computer device can be configured to execute instructions from a software application (e.g., an App) which controls health monitoring and collection of data from the wearable sensor device(s) 10. For example, an App can be one or more of an operating system (e.g., a Windows™ based operating system), browser application, client application, server application, proxy application, on-line service provider application, and/or private network application. The App can be implemented by utilizing any suitable computer language (e.g., C\C++, UNIX SHELL, SCRIPT, PERL, JAVA™, JAVASCRIPT, HTML/DHTML/XML, FLASH, WINDOWS NT, UNIX/LINUX, APACHE, RDBMS including ORACLE, INFORMIX, and MySQL). The App can comprise health, fitness, and/or physical movement analysis software. In some instances, the App can be downloaded to the device 116 from an external source, such as the external computer network 110. Following initial installation of the App, the device 116 can be configured to receive instructions, updates, or addition software from the external source either according to instructions included with the App or in response to a request from the external source.

In other examples, the intermediary device 116 is another medical, exercise, or patient monitoring device located in close proximity to the subject. For example, various types of exercise and medical equipment may include microprocessors for controlling device function. Instructions for receiving, processing, and providing feedback about sensed movement information from the one or more wearable sensor device(s) 10 can be loaded or downloaded to any such devices for implementing the patient monitoring and feedback systems discussed herein.

Controller

In some examples, the intermediary device 116 comprises a controller 118 for executing functions related to receipt, analysis, and transmission of sensed movement data. In some examples, a controller is a central processing engine including a baseline processor, memory, and communications capabilities. For example, the controller 118 can be any suitable processor comprising computer readable memory 120 and configured to execute instructions either stored on the memory 120 or received from other sources. Computer readable memory 120 can be, for example, a disk drive, a solid-state drive, an optical drive, a tape drive, flash memory (e.g., a non-volatile computer storage chip), cartridge drive, and control elements for loading new software.

In some examples, the controller 118 includes a program, code, a set of instructions, or some combination thereof, executable by the device 116 for independently or collectively instructing the device 116 to interact and operate as programmed, referred to herein as "programming instructions". In some examples, the controller 118 is configured to issue instructions to one or more of the wearable sensor devices 10 to initiate data collection and to select types of measurement information that should be recorded. In other instances, the wearable sensor device(s) 10 is configured to automatically transmit all sensed movement data to the intermediary device 116 either in real time or at periodic intervals without first receiving initiation instructions from the controller 118 to initiate sensing and data transmission.

In either case, as will be discussed herein, the controller 118 is configured to receive and process movement information from the wearable sensor device(s) 10 for activities performed by the subject. Processing can include applying filters and other techniques for removing signal artifacts, noise, baseline waveforms, or other items from captured signals to improve readability. As discussed in greater detail in connection with the discussion of FIGS. 3 and 4, processing information includes data analysis techniques, such as quantifying various movement parameters based on received data, corroborating or calibrating data from multiple sources, and/or analyzing generated movement parameters to draw conclusions about the subject.

In one example for analyzing received data, the controller 118 is configured to compare one or more inertial data sets obtained from the wearable sensor device(s) 10 with reference data comprising one or more reference inertial data sets stored on the computer readable memory or received from external sources, such as the computer network 110. For example, the reference inertial data sets can be stored on the storage device 114 and transmitted to the intermediary device 116 via the computer network 110. In some examples, the reference inertial data sets include average parameter values or target parameter values for individuals having similar physical characteristics to the subject. The controller 118 can be configured to determine one or more deviations, if any, between the inertial data set(s) and the reference inertial data set(s), and, if one or more deviations is present, generate a list of one or more activities or actions (e.g., a recommended treatment regimen) that the subject could perform as a corrective measures to address the identified deviations between the subject's inertial data set and the average or target data set for similarly situated individuals. Possible corrective actions, in the form of a treatment regimen or treatment protocol, can also be stored on a database on the storage device 114 and transmitted to the intermediary device 116 by the computing network 110 when required.

Communications Module

In some examples, the intermediary device 116 comprises a communications module 122 associated with the controller 118. In that case, the controller 118 is configured to cause the communications module 122 to transmit the raw, processed, or analyzed data from the wearable sensor device(s) to remote sources, such as the external computer network 110. In other examples, the data is uploaded from the intermediary device 116 to an Internet webpage or other remotely accessible database.

The communications module 122 comprises a short range data transceiver for communication with the communications module (shown in FIG. 2) of the wearable sensor device(s) 10. For example, the short range data transceiver may be a Bluetooth® transceiver, Zigbee transceiver, or similar data transmission device, as are known in the art. In other examples, the short range data transceiver can be a radio-frequency (RF) near-field communication device. In other examples, the communications module 122 comprises a wired data transmission interface. In that case, the wearable sensor device 10 can be connected to the intermediary device 116 using a USB cable or similar data transmission cable. The communications module 122 can also include a long-range wireless data transceiver 124 for communication with the computers 112 of the external computer network 110. For example, long range data transmission can use WiFi, cellular, radio frequency, satellite, and other known data transfer devices and protocols. Communication between the wearable sensor device(s) 10, the external computer network 110, and, if present, the intermediary device 116 can be encrypted by any useful method. In that case, the communications module 122 can be configured to receive encrypted data from the wearable sensor device 10 and process the encrypted data to remove encryption so that the received device can be analyzed. The communications module 122 can also be configured to encrypt data prior to long-range data transmission to the external computer network 110. For example, the devices 10, 112, 116 can use encryption, data redaction, and/or security mechanisms to ensure data privacy and that the system comports with privacy standards, such as the U.S. Health Insurance Portability and Accountability Act (HIPAA) standards.

Input/Output Components

In some examples, the intermediary device 116 further comprises an input component 126 and an output component 128 in communication with the controller 118, which allow the user to interact with and receive feedback from the intermediary device 116. The input component 126 includes one or more of a keyword, touchpad, computer mouse, trackball, or other data entry accessory, as are known in the art. In other examples, input components 120 include a microphone for capturing audio data entry by a user or optical or motion sensors for capturing gestures performed by the user. The input component 126 can be used to enter information about the subject which can be used to analyze the measurement data and/or to assist in determining injury risks or appropriate treatment regimens. For example, information about the subject's gender, age, height, weight, activity level (e.g., recreationally active, occupationally active, elite athlete), and other relevant information can be entered via the input component 126. The input components 126 can also be used to interact with a user interface by, for example, being able to toggle through instruction screens for positioning the wearable sensor device 10 on the subject and for performing different types of activity assessments. User interface screens that can be shown on a visual display and used for entering information and guiding a user in collecting information about a subject are shown in FIGS. 6A to 6E and discussed herein.

In some examples, the input/output components 126, 128 is a touch-screen display. In other examples, output components 128 includes a visual display, speakers, haptic output devices, and/or other types of feedback devices as are known in the art. The output component 128 can provide feedback to the clinician or subject about the subject's physical condition and, in particular, predictive injury information determined based on movement information captured by the sensor device 10.

In addition to providing feedback, in some examples, the controller 118 is configured to cause the output component 128 to provide visual or audio instructions to the user or subject about placement of the wearable sensor device(s) 10. In some examples, the intermediary device 116 also provides instructions to a user or to the subject related to the movement assessment being performed. In some examples, the intermediary device 116 displays visual images or animations on a device display guiding the rescuer in performance of specific assessment activities.

The components of the wearable sensor device 10, intermediary device 116, and external computer devices 112 can be combined in various manners with various analog and digital circuitry, including controllers, filters, ADCs (analog-digital chips), memory, communication devices and/or adaptors. Especially, but not exclusively with respect to the wearable sensor device 10, as devices become smaller and processors become more powerful and use less energy, it is possible to integrate many more sensors, such as MEMS or NEMS (microelectromechanical or nanoelectromechanical systems), onto single chips. MEMS accelerometers, gyroscopes, gas sensors, thermometers, humidity sensors, and magnetometers, are readily available from commercial sources and/or are abundantly described in the art. Technologies such as package on package (PoP) and system on a chip (SoC) integrated circuit packages allow manufacture of very small devices with significant capacities. For example, smart phones use PoP technologies to stack memory and processors in a very small volume. One example of a SoC is a microcontroller (MCU), which is a small computer on a single integrated circuit typically containing a processor core, memory, and programmable input/output peripherals. Microcontrollers also may include timer module(s) and analog-to-digital converter(s) for, e.g., converting analog sensor output to a digital signal.

External Database

With continued reference to FIG. 2, in some examples, the intermediary device 116 is in communication with the storage device 114 of the external computer network 110. For example, the intermediary device can receive information including subject information and reference data sets from databases stored on the storage device 114. For example, the storage device 114 can comprise a database of patient electronic health records for subjects. A health record contains personal information for the subject such as a subject's name, age, weight, height, body mass index (BMI), and blood pressure. A health record can also contain information about assessments previously performed by the subject or about a subject's history of past injuries. The intermediary device 116 can, for example and without limitation, store, communicate the personal information, and combine the personal information with the inertial data set information for communication to other external computer devices, such as the computer device 112. In some examples, the intermediary device 116 is also configured to redact private information from the personal information prior to communication of the personal information. The received patient information is used by the computer device 112 to improve analysis of the sensed movement information.

The storage device 114 can also comprise a database of reference data sets with movement information for a wide range of subjects. The database can be used to obtain reference datasets for other individuals with similar characteristics (e.g., physical characteristics, occupational or activity level, and/or injury history) as the subject. Physical measurements for the subject can be compared with reference data sets for improve specificity and accuracy in injury prediction. In some instances, reference data sets are based on average values for segments of a population (e.g., segments of the overall population with physical characteristics similar to the subject) or for the population generally. In other examples, a set of reference data sets is provided from the database for individuals with varying degrees of physical injury. In one example, the database includes a reference data set for an uninjured individual (no injury history), an uninjured individual (with history of prior injuries), a moderately injured individual, and a severely injured individual. In some examples, reference data sets included in the database are stratified by injury location and/or injury classification so that, for example, an inertial data set for an individual with an ankle sprain can be compared to reference data for a group of other individuals who also have an ankle sprain. The measured inertial data set for the subject can be compared to inertial data sets for the different injury levels to assess which injury level most closely matches the subject. In some examples, the database is organized to include multiple reference data sets for members of a team or for individuals with the same occupation. In that case, the subject's results are compared with other members of the team or occupation group to assess whether the subject is at higher injury risk, normal injury risk, or low injury risk compared with the other team or group members. As movement information for different subjects is obtained, processed, and analyzed, the database can be expanded to improve specificity and accuracy in injury prediction.

An accelerometer based approach to balance was considered in connection with force plate measures of balance within the Neuromuscular Research Laboratory in the technical article Heebner, et al., "Reliability and validity of an accelerometry based measure of static and dynamic postural stability", *Gait Posture* (2014) (hereinafter "Heebner"). An accelerometer based approach for assessing shear force during jumping is discussed in Sell, et al., "Relationship between tibial acceleration and proximal anterior tibia shear force across increasing jump distances", J. App. Biomechanics, 30: 75-81 (2014) (hereinafter "Sell"). Heebner and Sell are incorporated by reference herein in their entireties, to the extent of their disclosures and in a manner consistent with the present disclosure. The accelerometer measurements described in Heebner and Sell may be used as data entries for the database of reference values described herein.

Information Collection Processes

Figure 3:
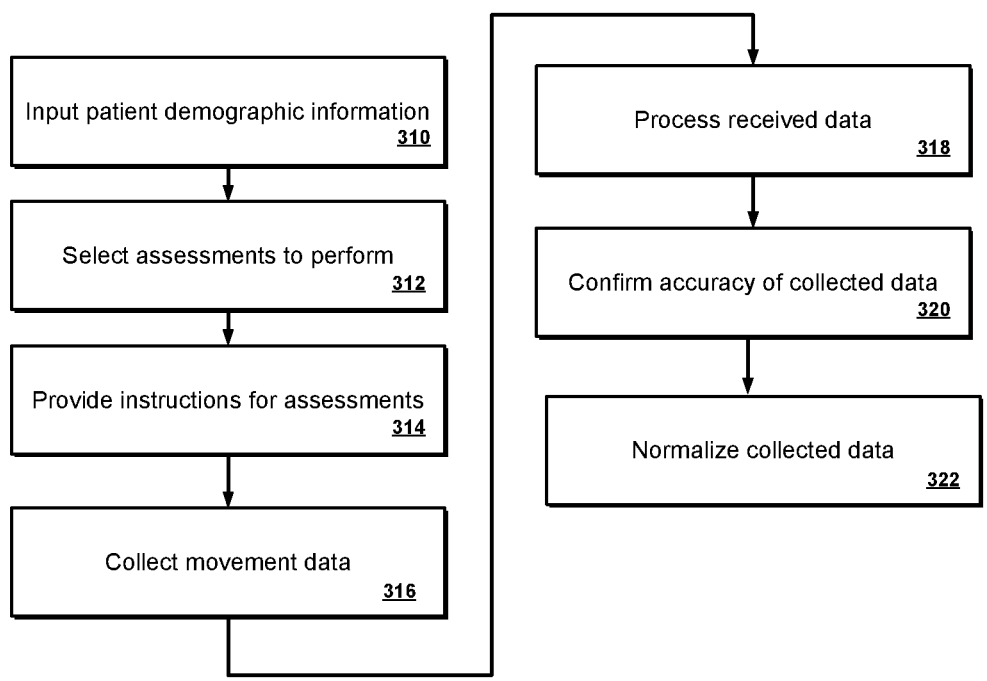
FIG. 3 is a flow chart of a process for data collection from a wearable sensor device with an inertial measurement unit according to an aspect of the disclosure.
Figure 4:
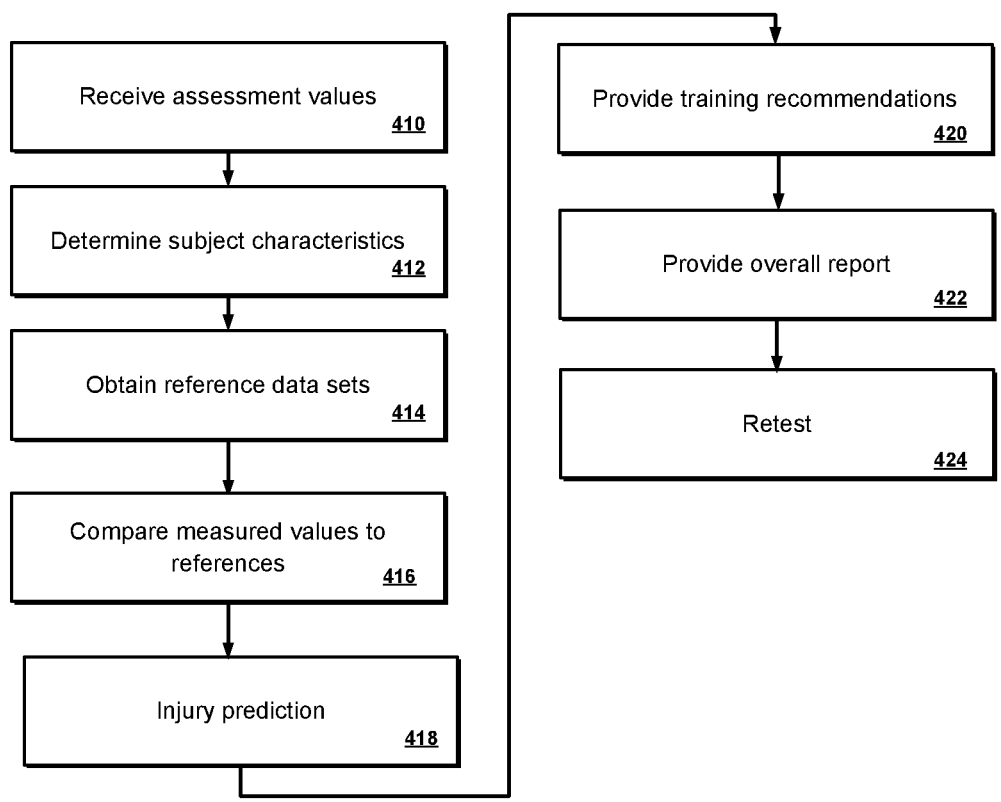
FIG. 4 is a flow chart of a process for analyzing an inertial data set obtained from a wearable sensor device, according to an aspect of the disclosure.

FIGS. 3 and 4 are flow charts illustrating processes for monitoring movement of the subject using the wearable sensor device, processing and analyzing information sensed by the sensor device, and providing feedback to a user and/or the subject about injury prediction and/or recommended treatment regimens. These processes are performed using the wearable sensor device(s), intermediary device, and external computer network shown in FIG. 2. The processing and data analysis techniques discussed herein can be performed by the intermediary device and/or by remote computer devices of the external computer network. In some instances, processing and data analysis functions are distributed between multiple computer processors on different devices. In one example, initial processing and data analysis is performed by the controller of the intermediary device. More sophisticated data analysis and reporting functions can be performed on remote computer devices of the external computer network (e.g., in the cloud).

As shown in FIG. 3, the wearable sensor device or intermediary device guides the user or subject through an initial setup process. In the example shown by box 310, during the setup process, the user is instructed to input patient demographic information about the subject's physical condition and other information. For example, in response to requests by the wearable sensor device or the intermediary device, the user or subject provides demographic information (e.g., age, weight, height, dominant limb) and/or activity level/type information for the subject. The activity type information can also include identifying a sport (e.g., baseball, softball, soccer, football, running, and lifting) performed by the subject. The subject can also be identified as a member of a particular group of interest. For example, the subject may identify that he or she is a member of a particular sports team or military branch and team. Assessment results for identified members of a group can be compared together during data analysis.

Based on the entered information, as shown at box 312, the wearable sensor and/or intermediary device is configured to select a battery of evidence-based assessments to collect movement data for the subject. For example, one or more musculoskeletal, biomechanical, physiological, neuromuscular, and/or performance assessments is selected. In some instances, the recommended assessments is selected for the purpose of identifying injuries that are common for individuals who perform the sport, occupation, or activity participated in by the subject. In other examples, the user manually selects which assessments are to be performed for the subject.

Exemplary musculoskeletal assessments include assessments of range of motion and flexibility of certain muscle groups and joints including, for example, the ankle, knee, hip, back, and/or shoulders. Assessments can also include an assessment of strength and endurance of the ankle, knee, hip, back, and/or shoulder musculature. Biomechanical assessments include, for example, an assessment of joint kinematic and kinetic data for the ankle, knee, hip, back, and/or shoulders, including maximum values or ranges of values for angles of movement, movement velocities, and accelerations, or for impact forces and ground reaction forces experienced during sport, military training, occupational, and common daily activities. Physiological assessments include, for example, assessments of anaerobic and/or aerobic capacity and power. Neuromuscular assessments include, for example, assessments of one or more of the following: lower extremity, upper extremity, and/or back motor control; balance and/or postural stability including dynamic postural stability; and joint coordination. Performance assessments include, for example, determining a subject's maximum jump height and/or horizontal jump distance, as well as determining the subject's lower extremity, upper extremity, and whole body work and power, agility, and/or running speed.

As shown at box 314, once the assessment is automatically selected or manually entered, the wearable sensor or intermediary device is configured to provide instructions to the user or subject for performing actions and collecting data relevant to the selected assessment. As an initial step, the device can provide instructions for correct placement of one or more wearable sensor devices on the subject for the selected assessment(s). In some instances, a user, such as a clinician, uses and controls the intermediary device. In that case, the clinician can view the guidance and instructions provided on the device and help the subject to properly place the sensor device(s) based on the viewed instructions. In one example, the clinician instructs the subject to strap the sensor device around a portion of his/her body such as the subject's wrist, arm, or waist. In other cases, instructions for performing the assessment are provided to the subject directly. In some instances, the clinician or subject is required to confirm proper sensor placement. In one example, the user or subject is required to tap an appropriate portion of the device touch screen after each sensor is placed to confirm placement. In other examples, the subject is instructed to perform an action (e.g., wave arm, clap hands, stomp foot) to confirm that movement data is being collected by the wearable sensor device in an expected manner.

Once placement of the wearable sensor device(s) is confirmed, the intermediary device can provide instructions for performing specific tasks or actions as movement data is being collected. For example, as discussed herein, during balance assessments, the subject is required to stand on one leg, hop up and down, or leap a specified distance and hold his/her landing position.

As shown at box 316, data collection occurs as the subject performs the instructed actions or tasks for each selected assessment. The obtaining of data includes obtaining one or more inertial data sets as the actions are performed. In one example, an inertial data set includes raw signals for acceleration rate, change of direction, rate of change of angles, or changes in force received from the accelerometer(s) and/or gyroscope(s) of the inertial measurement unit. In some instances, multiple inertial data sets are obtained by, for example, moving the wearable sensor device to another location on the subject's body and having the subject perform the action again. In other examples, multiple inertial data sets can be obtained simultaneously from wearable sensor devices disposed at different positions on the subject's body. In other examples, the subject is instructed to perform a first action followed by a second action. Data for each action is recorded by a single wearable sensor device.

In some instances, the intermediary device is configured to emit a visual cue to prompt the clinician or the subject that the subject is in the correct starting position and can begin the instructed action or task. In one example, a visual indicator on the wearable sensor device lights up to instruct the subject that he/she can begin the action or task. In other examples, a notification is presented on the intermediary device which can be acknowledged by the clinician or subject. In a similar manner, the user or subject confirms that the movement is complete and that data collection can cease. For example, for flexibility measures, the subject moves an extremity (arm or leg) through its range of motion as instructed until it reaches its stop point (e.g., maximum extension of the joint without pain). When the stop point is reached, the subject or clinician confirms the location of the stop point by, for example, selecting an appropriate indicator on the intermediate device. The setup and data collection steps can be performed repeatedly until all measurements for the selected assessments are obtained.

After one or more inertial data sets are obtained, as shown at box 318, the received signals are processed. In some instances, data processing is performed by the intermediary device. In other examples, data processing is performed by one or more remote computer devices of the external computer network. In that case, the monitoring device and/or intermediate device are configured to transmit obtained raw or processed data to the remote computer device(s) for processing and analysis. In some examples, processing of the raw signals includes filtering the received signals to remove artifacts or outlier values.

In some examples, as shown at box 320, collected or derived measures is assessed for accuracy and precision by determining if values are physically possible and/or repeatable. Raw data which produces physiologically impossible measurement values for certain physiological parameters is discarded as corrupt. In that case, the clinician or subject is prompted to perform the assessment again in hopes of obtaining accurate reasonable results. When all measurements are accepted by the user and/or device as being reasonable, as shown in box 322, additional calculations are made for improving analysis and information displayed to the user. In one example, calculations are performed on raw data from the inertial measurement unit to determine parameter values for flexibility, range of motion, balance, and others. The calculations can include, for example, normalizing measurements to a standardized metric (e.g., body-weight, height, etc.). In other examples, additional calculations include taking a ratio of a measure bilaterally and/or taking a ratio between agonist and antagonist muscle groups.

Some specific examples of techniques for quantification and/or normalization of received raw data for different assessments will now be described in detail. Computer pseudocode for transforming the received data is also included in some cases. It is understood that the provided pseudocode is merely one manner of transforming received raw data. Other processing routines or algorithms will also be envisioned by individuals of ordinary skill in the art.

Shoulder Internal Rotation

Measurements from the gyroscope of the inertial measurement unit can be used to determine shoulder internal rotation angle. Shoulder rotation angle refers to an angle or range of motion of the shoulder joint and is determined by identifying a stop point or point of maximum shoulder extension. Such measurements were previously determined using protractors or similar measurement devices for measuring rotation angle. Using the wearable sensor device, such measurements can be obtained automatically. In some examples, gyroscope data can be pulled into the following algorithm to find the shoulder rotation angle:

```
accelfs = 100; %HZ
angle = 0;
for i = 2:length (gyroData) %calculate angle from gyroscope data
    angle = angle + gyroData (i) * (1/accelfs) ;
    positionData (i) = angle;
end
last = length (positionData);
FinalAngle = round (positionData (last));
```

In some examples, as discussed herein, the internal shoulder rotation angle is compared to shoulder rotation angles for other individuals with similar physical or occupational characteristics to the subject. Similarly, the calculated internal shoulder rotation value can be compared to individuals with different degrees of shoulder injury to determine whether the subject appears to have or to be at risk for shoulder injury. Values for a second inertial data set are processed in a similar manner to obtain range of motion for another joint. In one example, data is collected and processed to determine shoulder external rotation. In other examples, a total arc of motion is calculated. Values for internal shoulder rotation, external shoulder rotation, and total arc of rotation can be considered together to provide a more detailed assessment of injury risk.

Dynamic Postural Stability

In another example, accelerometer data is used to access balance and postural stability of the subject. Initially, the subject is placed in a calibration position. For example, the subject can be prompted to stand in an upright position against a wall to limit movement, while 3 to 10 seconds of acceleration data are collected. In one example, the following algorithm is used to process the collected calibration data to correct or calibrate alignment of the sensor to a vertical-horizontal coordinate system:

```
accel_g = [0 0 g]; %desired gravity vector, sensing graviity is the z
direction
e = cross (AVGaccel_m, accel_g);
e_norm = e/ (norm (e));
alpha = acos (AVGaccel_m (3) /norm (AVGaccel_m));
q0 = cos (alpha/2);
q1 = sin (alpha/2) *e_norm (1);
q2 = sin (alpha/2) *e_norm (2);
q3 = sin (alpha/2) *e_norm (3);
%Transformation matrix
R = [(1-2* ((q2^2) + (q3^2))) (2*((q1*q2) - (q0*q3))) (2*((q0*q2) + (q1*q3))); ...
     (2* ((q1*q2) + (q0*q3))) (1-2* ((q1^2) + (q3^2))) (2* ((q2*q3) - (q0*q1))); ...
     (2* ((q1*q3) - (q0*q2))) (2* ((q0*q1) + (q2*q3))) (1-2* ((q1^2) + (q2^2)))];
```

After calibration data is obtained, the subject performs a physical action. For example, the action can be a forward jump, in which the subject takes off from two feet, jumps a distance of about 2 feet, and lands on one foot, while sticking the landing. The subject holds the landing position for about 5 seconds while data representative of balance or stability is collected. Taking one or more extra hops would be an invalid result. Accelerometer data is collected during the jump and for the first 3 seconds after landing. The following algorithm is used for identifying the landing point and the 3-second window:

```
% Transform accleration data to vertical-horizontal orthogonal
% coordinate system
for i = 1:length (accelData)
  acceltrans = R*accelData (i,:)';
  accelT (i,:) = acceltrans';
end
% Define axes for filtering
Taxis1 = accelT(:,1); %ML
Taxis2 = accelT(:,2); %AP
Taxis3 = accelT(:,3); %vertical
% Create Butterworth filter
[a, b] = butter (2,50/500); %accel filter
% Run filter
axis1 = filtfilt (a,b,Taxis1);
axis2 = filtfilt (a,b,Taxis2);
axis3 = filtfilt (a,b,Taxis3);
Acceldata = [axis1 axis2 axis3];
clear axis1 axis2 axis3 accelT Taxis1 Taxis2 Taxis3 accelData
% Calculations
[Vpeak, iVpeak] = max (data(clickedposition: length (data), 3));
[Vmin, iVmin] = min (data(clickedposition: length (data), 3));
if abs (Vpeak) < abs (Vmin)
  Vpeak = Vmin;
  iVpeak = iVmin;
end
% Calculate RMS from peak to +3 seconds
RMSx = rms (data(IPEAK: (IPEAK+ (3*fs_accel)),1));
RMSy = rms (data(IPEAK: (IPEAK+ (3*fs_accel)),2));
RMSz = rms (data(IPEAK: (IPEAK+ (3*fs_accel)),3));
RMSr = rms (data(IPEAK: (IPEAK+ (3*fs_accel)),4));
```

Average or mean acceleration derived values in the x, y, and z directions are considered for the three seconds following the landing to provide a quantitative indication of the subject's balance. The results can be compared to data for individuals with similar characteristics to the subject in the manner discussed above. The results of the comparison can be used to assess injury risk and for training recommendations.

Injury Prediction Analysis and Automated Treatment Recommendation

A process for analyzing the quantified or normalized values to provide feedback to the user or subject for injury prediction and treatment recommendation is shown in FIG. 4. As shown in FIG. 4, the obtained parameter values(s) are analyzed by comparing the derived values to measurements obtained from other subjects and stored in a database. In some examples, the other subject data includes average values based on measurements for a group of similarly situated individuals. In other examples, reference values are calculated or derived from data for the general population. In one example, a function of shoulder rotation angle with respect to subject age is derived from data for subjects of different ages. The reference values for shoulder rotation of the subject of interest are calculated from the derived function.

As shown at box 410, the process begins when the values for the measurements of interest are received. As described herein, the values are derived from movement data collected by the wearable sensor device(s) worn by the subject while performing the assessment(s). In one example, the received values include values derived from multiple data sets, such as a first inertial data set and a second inertial data set. The process also includes identifying characteristics of the subject so that reference values may be obtained, as shown at box 412. Subject characteristics include the subject's age, history of previous injuries, and/or the subject's activity level and/or level of occupational activity. In one example, this characteristic information is provided by the user or subject as discussed above. In other examples, subject information is automatically downloaded from a remote source, such as a patient health record.

As shown at box 414, benchmark or reference data sets are obtained from external sources, stored on one or more databases of the computer network, and downloaded to the computer device or intermediary device as needed. In one example, derived flexibility and balance measures are compared to benchmarks determined through analysis of collected normative data, e.g., data collected by the Neuromuscular Research Laboratory. Specific entries or values from the database or data set are selected based on the provided demographic in formation about the subject.

As shown at box 416, the measured reference values for the subject are then compared to the reference values from the database. The results of the comparison can be used to determine a derivation between the measured data and reference data sets. Comparison of one data set to another can be accomplished by any method, for example and without limitation, by differencing methods. A variety of other methods and data formats are amenable to such comparisons. For example, a computer process, such as a table, a matrix, a statistical representation, an object, an equation, an image, compressed data, and combinations thereof can be used in manners which are apparent to those of ordinary skill in the art.

As shown at box 418, the derived data set and/or results of the comparison between the data set and reference values are used for injury prediction. In one example, results of the comparison are used to derive algorithms that predict injury based on multiple confounding factors. For example, reference values can be viewed as cutoff points for injury risk associated with a certain assessment. Thus, if the subject's values for a particular assessment are below a predetermined range, the subject may be at low risk of a particular injury. If the subject's values fall within the range of average individuals, then the subject is determined to be at normal risk of a particular injury. If the subject's measured values exceed an upper limit of the range, then the subject is determined to be at high risk for an injury. Injury risk for each of the one or more assessments can be considered separately to give the subject information about injury risk for different muscle groups, joints, or extremities. In other examples, the subject's injury risk for multiple assessments are considered together to provide the subject with a single overall injury risk score that assesses and condenses the subject's overall risk of injury to a single score or metric.

Once areas at risk of injury have been identified, as shown at box 420, a list of recommended exercises is generated to improve muscles, muscle groups, or other parts of the subject's body having heightened injury risk. The generated list can be provided to the subject or clinician. In one example, the intermediary device is configured to provide one or more instructional videos explaining for the subject how certain exercises or activities are performed. It is believed that performing the recommended exercises in the proscribed manner decreases risk of injury from the identified factors. In other examples, a training recommendation includes an instruction for correctly performing an activity, task, or exercise along with a comprehensive explanation of a correct exercise technique. Training recommendations can be experimentally validated to modify identified injury risk factors.

As shown in box 422, a subject report is prepared from the collected and analyzed data. For example, assessment results, derived values, predictive injury information, and training recommendations generated based on collected data can be collected together into a formal report. In some examples, the report is provided on a visual display screen or touch screen of the intermediary device. The report can be a basic report which merely includes certain derived measures or a comprehensive report showing derived measures, associated risk, and training recommendations. For example, a comprehensive report can include a combination of raw data, graphs, and analyzed results, such as predictive injury information. In some examples, predictive injury information also includes a list of muscles, muscle groups, and other body areas at risk of injury. The report can also include numerical or other types of indicators visually showing injury risk. In one example, the indicator shows whether a specific muscle or muscle group is at low risk, medium risk, or high risk of injury. In other examples, risk of injury for muscle groups is shown graphically, such as in a color-coded image of a human body. Different portions of the image are shown in different colors corresponding to the estimated injury risk for that particular body region. Training recommendations can also be provided in the report, which are based on the determined risk associated with each assessment. In some examples, the comprehensive report includes comparing measurements for the subject, injury risk, and other results compared to a team average, team maximum, or team minimum to provide the subject or clinician with information about how he/she performs compared to peers.

Following a period of days or weeks, the subject is retested as shown at box 424, to assess whether training recommendations have reduced injury risk. Advantageously, because the sensing device is portable and wearable, measurements are taken on a semi-regular or periodic basis to assess progress in training and without requiring the subject to visit a lab location for each new assessment. Further, in some instances, training recommendations are updated or modified based on subsequent test results. Additionally, algorithms for generating treatment recommendations can be updated or improved based on collected measurements (e.g., through system learning, fuzzy logic, or neural network techniques) so that the longer the subject uses the sensing device, the more accurate and/or sophisticated the training recommendations can become.

Figure 5:
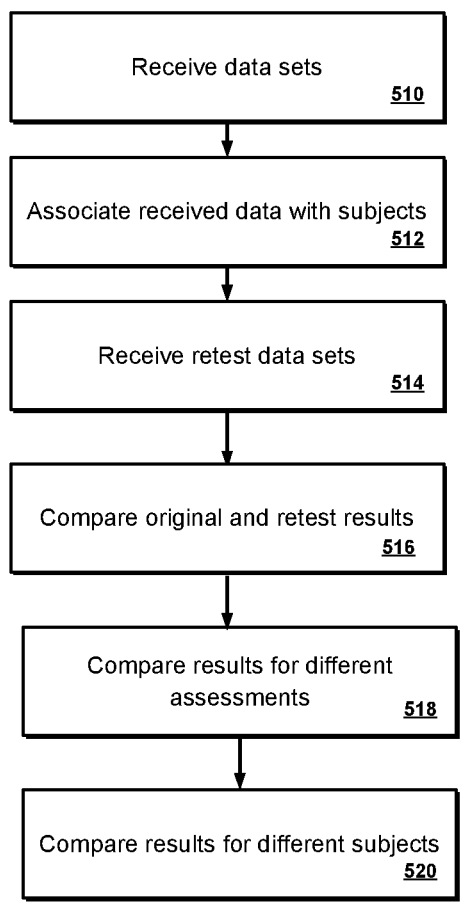
FIG. 5 is a flow chart of a process for receiving and providing feedback regarding movement information obtained from a plurality of wearable sensor devices worn by different subjects.

FIG. 5 shows a flow chart of a process for collecting information from sensor devices worn by multiple individuals, processing the collected information, and providing feedback related to subject outcomes and treatment success rates based on the accumulated information. As shown at box 510, raw signals in the form of inertial data sets are received by a computer device of the external computer network from a plurality of wearable sensor devices worn by different subjects. In some instances, the data sets are from different subjects performing the same assessments simultaneously. In other examples, the received signals are for different types of assessments or for assessments performed at different times and/or at different locations.

As shown at box 512, the computing device is configured to associate the received data sets with respective subjects. In some examples, the received information also includes predictive injury information and treatment recommendations for the subject. In some cases, the received data sets include identifying information for the respective subject. For example, identifying information can include subject physical characteristics. Identifying information can also include information about the clinician, therapist, or facility responsible for treating or testing the subject. In some instances, associating the received information with the respective subject can include processing the data to determine the patient information and storing the received data in computer memory or a database organized according to received information about the clinician, therapist, or facility. In some examples, information stored in the database is modified to remove patient identifying information, such as a patient's name. In this way, results information for multiple subjects can be compared and analyzed while preserving patient anonymity.

As shown in box 514, after a period of time, the computer device receives retest information for the different subjects. Results of retests are used to assess accuracy of injury prediction information and success or failure of the different treatment regimens. For example, as shown at box 516, the originally received parameter or metric values are compared to values received for retests to assess a degree of deviation between the original and retest data. Little or no deviation indicates that the treatment regimen has not led to improvement, but that any underlying physical conditions have not worsened over time. A decrease in quality of received values indicates that the subject was injured between when the original data was received and the retest. An increase in the quality of data indicates that the treatment regimen was effective. As shown at box 518, results for multiple assessments are compared to identify any correlations between different subjects. For example, a correlation can be found between related muscles or muscle groups indicating that an injury to one muscle also resulted in deteriorating results for the related muscles or muscle groups.

As shown at box 520, the degree of deviation between the original results and the retest results are compared for different subjects to assess whether the treatments suggested by certain clinicians, therapists, or healthcare facilities are effective. For example, an average degree of improvement or deterioration can be calculated for all subjects treated by a clinician. The degree of improvement or deterioration can be compared to results for other clinicians who work with similar patients (e.g., patients having similar physical characteristics or activity levels) to determine whether some clinicians have a better success rate than others. In other examples, success or deterioration rates for different healthcare facilities is compared to assess overall effectiveness of entire facilities.

User Interface

With reference to FIGS. 6A to 6E, screens for a user interface for setting up, using, collecting information from a wearable sensor device and for providing feedback to a user or subject are illustrated. In some examples, the user interface screens shown in FIGS. 6A to 6E are displayed on an intermediary device, such as a smart phone, tablet, or personal digital assistant (PDA) device.

Figures 6A, 6B:
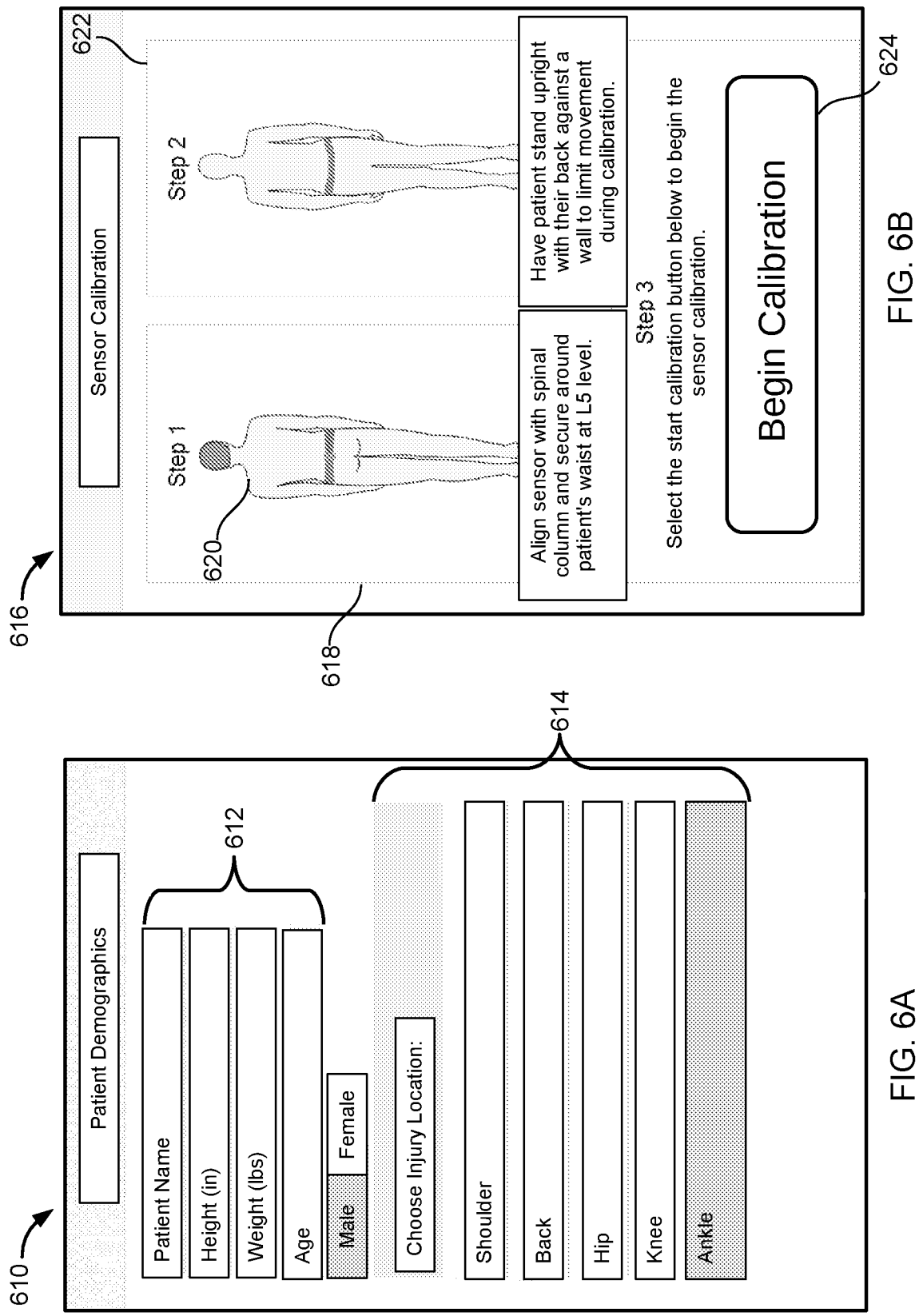
FIGS. 6A to 6E are screen captures for an exemplary user interface for use with the movement analysis system of FIG. 2.

As shown in FIG. 6A, the user or subject is presented with an initial screen 610. The screen includes a patient demographic section 612 for entering general information about the subject including: name, height, weight, age, and gender. The initial screen 610 also includes a section for the user to manually enter a body region that will be assessed. For example, the user can select the shoulder, back, hip, knee or ankle. FIG. 6B shows a sensor calibration screen 616. As shown by the "Step 1" section 618, instructions are provided for placement of the wearable sensor device. The instructions can include an image 620 or animation of a person wearing the wearable sensor device to assist in placement. As shown in the "Step 2" section 622, instructions for calibration of the wearable sensor device are provided. In this example, the subject is instructed to stand upright against a wall and remain as motionless as possible. Once the subject is in position, the user selects the begin calibration button 624 to begin collection of calibration data.

Figure 6D:
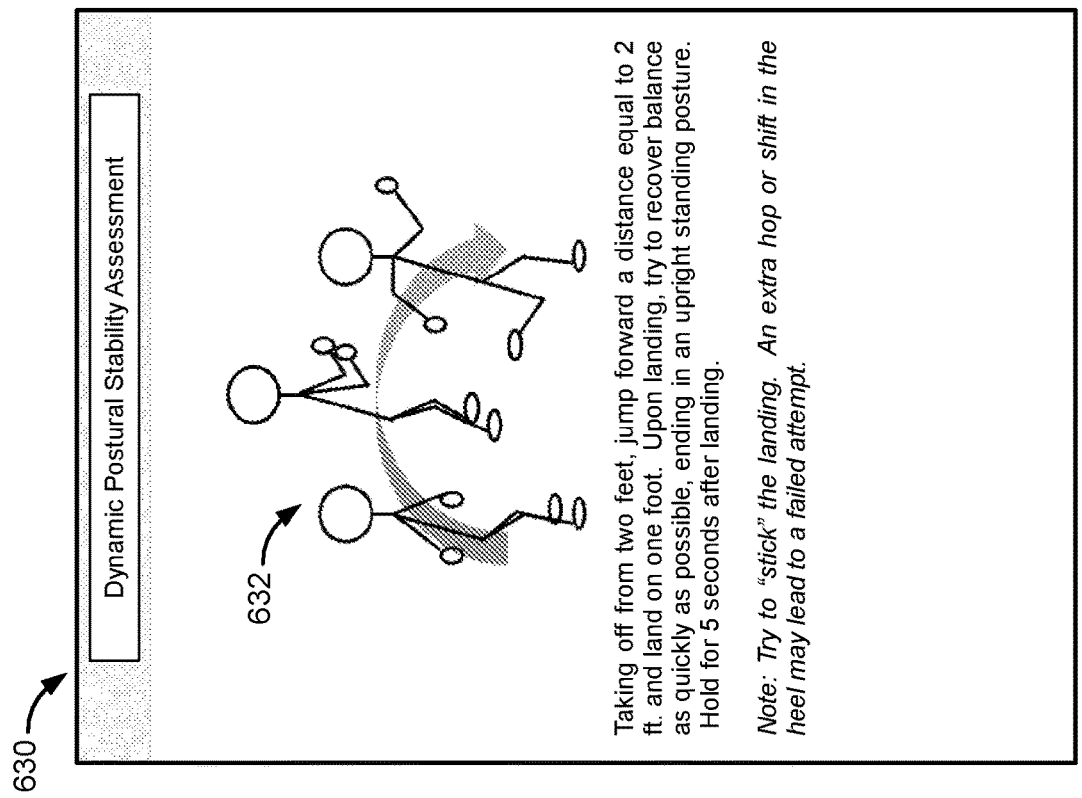
Figure 6C:
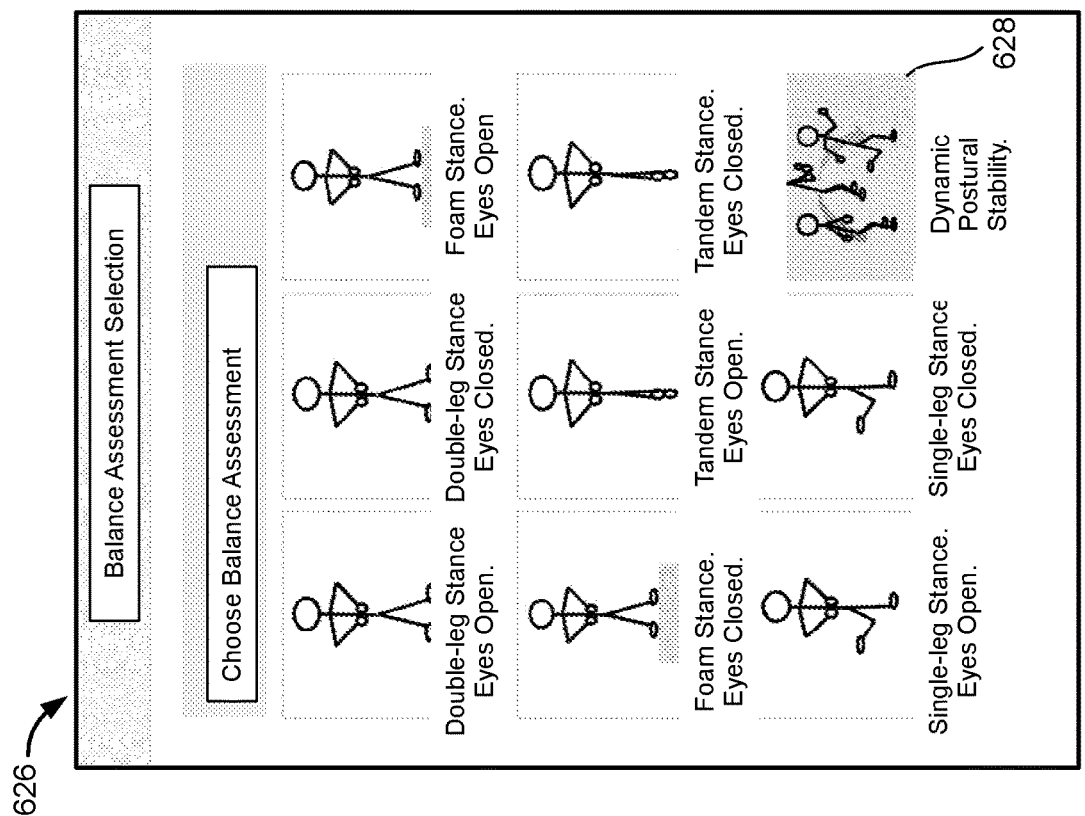

As shown in FIG. 6C, a balance assessment selection screen 626 is illustrated, which allows the user to select an action to be performed by the subject from a list of possible actions. In this example, the actions include static balance assessments including, for example, standing on both legs (eyes open or closed) or standing on one leg (eyes open or closed). The list also includes a dynamic postural stability assessment option 628. As shown in FIG. 6D, if dynamic postural stability is selected, the user is provided with an instruction screen 630 for the dynamic postural stability assessment. In the dynamic postural stability assessment, the subject is instructed to jump, taking off with two feet and landing with one foot, as shown by the image 632 in FIG. 6D. After landing, the subject is instructed to regain his/her balance and stand on one foot for at least 5 seconds as data is being collected.

Figure 6E:
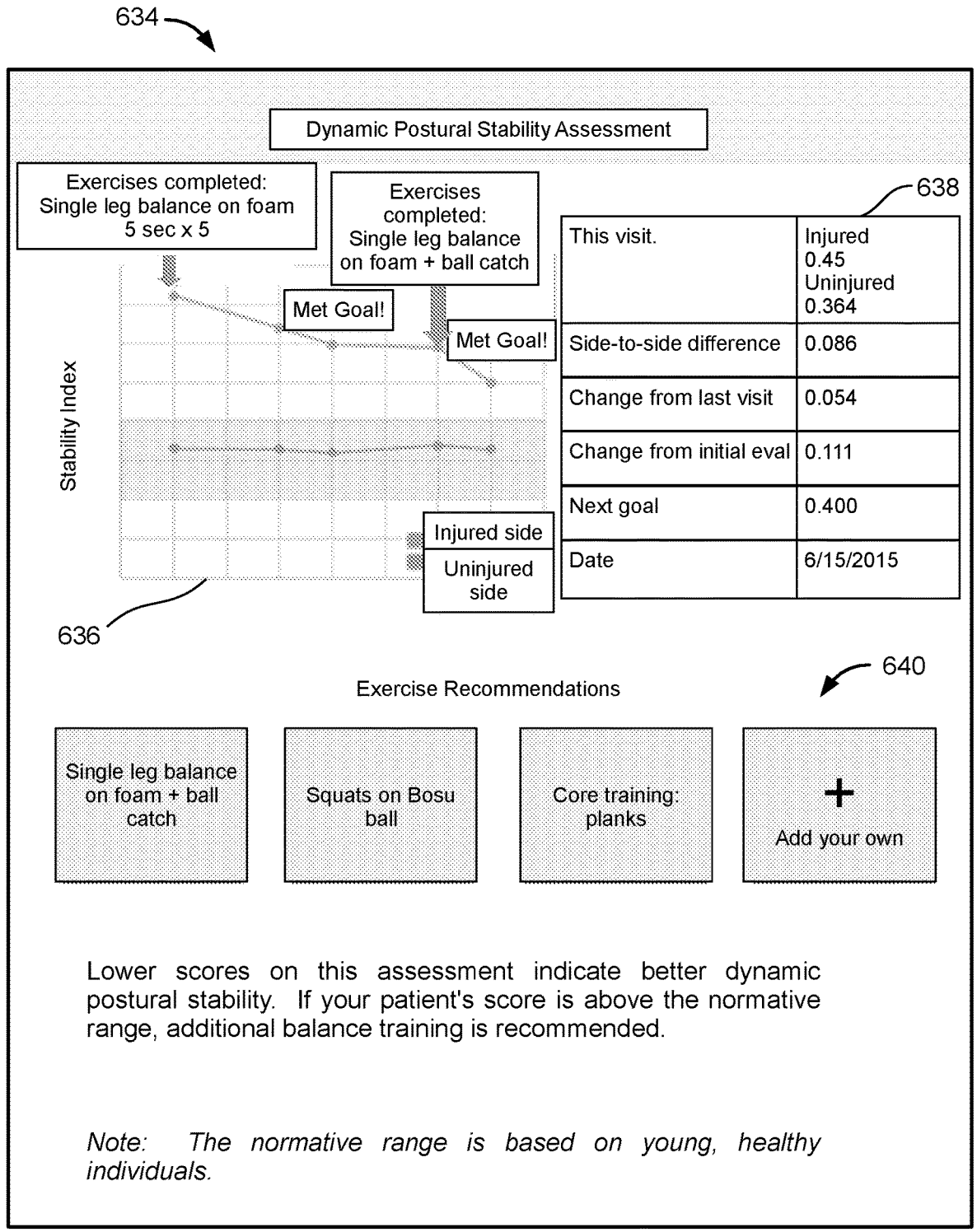

As shown in FIG. 6E, a report screen 634 with results from the dynamic postural stability assessment is illustrated. The screen 634 includes a graph 636 showing the subject's stability index for assessments taken on different days. The graph 636 compares results for a subject's injured side and uninjured side. The screen 634 also includes a data table 638 showing comparisons between the subject's injured side and uninjured side for a particular assessment. Data for side to side differences, changes from a previous visit, changes from an initial evaluation, a future goal, and other parameters is shown in the table 638. The screen 634 also includes an exercise recommendation section 640. Training recommendations for improving balance and/or postural stability can include, for example, instructing the subject to balance on one leg (possibly while standing on a foam support) and catch a ball, practicing squats, and/or core training exercises.

EXAMPLES

Example 1: Shoulder Internal Rotation

An exemplary process for assessing shoulder internal rotation using the wearable sensor device will now be described. Initially, demographic information for the subject is entered in the manner described herein. For example, patient name, height, weight, age, and sex are entered using a computer or mobile device. The entered demographic information can be sent to a remote server either immediately or at a later time. The user then selects the body region to be assessed. For example, the user can select the shoulder from a list of possible alternative joints and muscle groups. The user then selects the type of assessment to be performed. Assessments that can be used to test shoulder function and stability include obtaining measurements for range of motion/flexibility, strength, joint kinematics, and joint coordination. In this example, the user chooses range of motion. The user is then shown a list of possible range of motion measurements that can be taken at the selected joint. Possible measurements include measuring internal shoulder rotation, external rotation, flexion, extension, and posterior shoulder tightness. In this example, the user selects to perform an internal shoulder rotation assessment. The user or subject is then shown instructions or a description of how to perform the assessment.

To test internal shoulder rotation, the user is given instructions on where to place the wearable sensor device and how to secure it to the subject's arm. In this example, the wearable sensor device is secured with a strap to the subject's forearm, so that the z-axis measured by the accelerometer of the inertial measurement unit is aligned with the subject's ulna. Once the wearable sensor device is in place, the subject is placed in a starting position. For example, in the starting position, the subject can be lying supine with the upper arm laterally flexed to 90 degrees and the lower arm flexed to 90 degrees.

Once the subject is correctly positioned, the user or subject is prompted to start data collection by, for example, touching an appropriate portion of the touch screen of the intermediary device. When data collect commences, the subject moves the arm and shoulder through a range of motion until a stop point is reached. For example, the subject's forearm can be guided in an arcing motion towards the subject's feet while keeping the upper arm stable. This forces the shoulder into internal rotation.

Once the arm reaches the stop point, data collection ceases based either on a timer (e.g., data is only collected for a short period of time) or when the user performs an action to cease data collection, such as pressing an appropriate button on the intermediary device. After data collection is complete, gyroscope data for the arm movement is obtained from the wearable sensor device and analyzed to identify a final angle or position in the manner discussed herein. Once calculated, the angle position data point is sent to the external server to be stored in a database. The angle position data can also be compared to reference data for subjects having similar characteristics (age, gender, injury history) to assess for injury risk. In some cases, the database provides specific injury profiles indicating that when a subject's value is worse than a predetermined target value, the subject is at greater risk for injury. When the predetermined target value is not available or when a unique population, without sufficient reference data, is being studied, a value is calculated that can "red flag" an individual for injury risk. Based on a population mean, this "red flag" value can be set as being a lower worst quartile value determined based on measured data for a population.

Once the overall angle or rotation value and injury prediction information are obtained, the angle value is displayed to the user or subject on a display screen of the intermediary device. In addition, visual indicators are provided adjacent to the displayed valued. For example, a green icon may indicate that the calculated angle is within an expected range and that injury risk is low. A red icon can indicate that injury risk is high and that precautions to reduce injury to the assessed muscle or muscle-group should be taken.

After data analysis is complete, the user or subject is prompted with possible exercises (e.g., a treatment regimen) to improve the variable that was assessed. In this example, the user receives a recommendation to periodically perform a sleeper stretch as a potential exercise to improve shoulder internal rotation. When multiple shoulder range of motion assessments are performed, for example internal rotation and external rotation, additional calculations are made to derive another data point. In this example, total arc of motion may be derived from measured data, which is another parameter that can be stored in the database and referenced for injury risk.

Example 2: Dynamic Postural Stability

In an initial step, the user or subject inputs demographic information including patient name, height, weight, age, and sex for the subject using a computing or mobile device, in the manner described herein. After the demographic information is entered, the user or subject is asked to select a body region to be assessed. To measure dynamic postural stability, the user selects between the ankle(s), knee, hip, or back as balance is related to each of these joints. In this example, the user selects the ankle. The user is then prompted to select an assessment to perform from a list of tests and assessments, which are relevant to the ankle. Relevant tests include measuring range of motion/flexibility, strength, joint kinematics, joint coordination, and/or balance. In this example, the user chooses balance.

The user or subject is then given instructions for placement of the wearable sensor device and for securing the device to the subject's body. In this example, the wearable sensor device is secured with a strap to the subject's waist, so that the z-axis is aligned with the subject's spine and the center of the device is positioned over the L5 vertebra.

Once the wearable sensor device is in place, the subject is placed in a calibration position. In this example the subject is prompted to stand in an upright position against a wall to limit movement. Once the subject is in position, 3 to 10 seconds of acceleration data is collected. A calibration algorithm is derived from the collected data to correct alignment of the sensor to a vertical-horizontal coordinate system. An exemplary calibration algorithm than can be used for accelerometer data is described herein in connection with the description of FIG. 3.

The user or subject is next provided with a list of possible balance measurements that are taken by the wearable sensor device. In this example, the user or subject selects from one or more of the following: double leg static stance with eyes open or with eyes closed; double leg static stance on a foam pad with eyes open or eyes closed; tandem static stance with eyes open or eyes closed; single leg static stance with eyes open or eyes closed; and dynamic postural stability. In this example, the user selects dynamic postural stability.

The user or subject is then provided with instructions for performing the dynamic postural stability assessment. As described in previous examples, the dynamic postural stability assessment includes jumping, landing on one foot, and holding the landing for a short period of time (e.g., about 3 seconds) while movement data is collected. In some instances, the user is required to select a start button as the subject starts to jump to initiate data collection. The collected accelerometer data is analyzed to separate data for the jump from data for the 3 seconds after landing. The data for the 3 second after landing is analyzed, as previously described, to determine average movement or acceleration derived values (e.g., RMS information) for each axis. The calculated RMS values for the x, y, and z axes can be compared to reference data sets, as previously described, to determine feedback including predictive injury information and recommended training regimens for the subject. The feedback is provided to the user and/or subject by the computing or mobile device.

While several examples and embodiments of the wearable sensor device, movement analysis and assessment system, and processes for providing predictive injury information based on sensed movement data are shown in the accompanying figures and described hereinabove in detail, other examples and embodiments will be apparent to, and readily made by, those skilled in the art without departing from the scope and spirit of the invention. For example, it is to be understood that this disclosure contemplates that, to the extent possible, one or more features of any embodiment can be combined with one or more features of any other embodiment. Accordingly, the foregoing description is intended to be illustrative rather than restrictive.

Preferred and non-limiting aspects or embodiments of the present invention will now be described in the following numbered clauses:

Clause 1: A neuromuscular, physiological, biomechanical, or musculoskeletal activity monitoring system for a subject, the system comprising: a wearable inertial measurement unit comprising at least one accelerometer and/or at least one gyroscope, the inertial measurement unit being configured to be worn by the subject; and a controller in communication with an output component, the controller configured to: receive and process information from the inertial measurement unit representative of one or more physical actions performed by the subject; generate an inertial data set for the one or more physical actions based on the received and processed information; compare the generated inertial data set to reference data stored on computer readable memory in communication with the controller; and cause the output component to provide feedback comprising predictive injury information, the predictive injury information being based, at least in part, on the comparison between the generated data set and the reference data.

Clause 2: The system of clause 1, wherein the one or more actions comprise actions for one or more of a musculoskeletal assessment, a biomechanical assessment, a physiological assessment, a neuromuscular assessment, and a performance assessment.

Clause 3: The system of clause 1 or clause 2, wherein the one or more actions comprise actions for a dynamic stability assessment, the actions comprising performing a jump and holding a landing for a predetermined duration.

Clause 4: The system of any of clauses 1 to 3, wherein the predictive injury information comprises an indication of whether the individual has a low risk of injury, a moderate risk of injury, or a high risk of injury.

Clause 5: The system of any of clauses 1 to 4, wherein the reference data comprises one or more reference inertial data sets for the one or more physical actions performed by the subject.

Clause 6: The system of any of clauses 1 to 5, wherein comparing the generated inertial data set to the reference data comprises determining a deviation between at least a portion of the generated inertial data set and the reference data, and wherein the predictive injury information is based on a magnitude of the deviation.

Clause 7: The system of any of clauses 1 to 5, wherein comparing the generated inertial data set to the reference data comprises comparing the generated inertial data set to a reference inertial data set for an uninjured individual and comparing the generated inertial data set to a reference inertial data set for an injured individual.

Clause 8: The system of any of clauses 1 to 7, wherein the feedback further comprises a recommended training regimen for the subject selected based, at least in part, on the comparison between the generated data set and the reference data.

Clause 9: The system of clause 8, wherein the training regimen comprises one or more of stretching, strength building actions, and aerobic or anaerobic exercises.

Clause 10: The system of any of clauses 1 to 9, wherein the generated inertial data set comprises values for one or more of acceleration, velocity, angular momentum, rotation, and force.

Clause 11: The system of any of clauses 1 to 10, wherein the controller is configured to cause the output component to provide instructions to a user for placing the inertial measurement unit on the subject.

Clause 12: The system of any of clauses 1 to 11, wherein the controller is configured to cause the output component to provide instructions to a user or to the subject for performing the one or more physical actions, and wherein the information from the inertial measurement unit is collected as the one or more physical actions are being performed.

Clause 13: The system of any of clauses 1 to 12, further comprising an input component in communication with the controller, wherein the controller is configured to receive subject demographic information about the subject entered via the input component.

Clause 14: The system of clause 13, wherein the subject demographic information comprises one or more of subject height weight body mass index, occupation, activity level, and injury history.

Clause 15: The system of clause 13 or clause 14, wherein the feedback comprising predictive injury information is based, at least in part, on the received subject demographic information.

Clause 16: The system of any of clauses 13 to 15, wherein the reference data are selected from a database of representative data sets, the selection being based, at least in part, on the received subject demographic information.

Clause 17: The system of any of clauses 1 to 16, wherein the controller is configured to compare values of the generated inertial data set to maximum physically possible values, and to provide a notification via the output component if the maximum physically possible values are exceeded.

Clause 18: The system of clause 17, wherein the notification comprises an instruction to perform the one or more actions over again to obtain new data.

Clause 19: The system of any of clauses 1 to 18, wherein the controller is associated with an intermediary device, the intermediary device comprising: a first wireless transceiver for receiving information from the inertial measurement unit; a second wireless transceiver for transmitting processed information to an external computer network; and a visual display for providing feedback to the user.

Clause 20: The system of clause 19, wherein the intermediary device comprises one or more of a portable computer device, a cellular telephone device, a web-enabled telephone device, a smartphone, a tablet, and a personal digital assistant device.

Clause 21: The system of any of clauses 1 to 20, wherein the inertial measurement unit comprises three orthogonally positioned accelerometers for measuring acceleration along the x, y, and z axes.

Clause 22: The system of clause 21, wherein the inertial measurement unit further comprises three gyroscopes oriented along the x, y, and z axes respectively.

Clause 23: The system of any of clauses 1 to 22, configured to perform one or more aspects of Example 1 or Example 2.

Clause 24: A method of monitoring neuromuscular, physiological, biomechanical, or musculoskeletal activity of a subject, the method comprising: placing an inertial measurement unit comprising at least one accelerometer and/or at least one gyroscope on the subject; obtaining information representative of one or more inertial data sets from the inertial measurement unit during one or more physical actions performed by the subject; comparing the generated one or more inertial data sets to reference data for the one or more physical actions; and determining predictive injury information for the one or more physical actions performed by the subject, the predictive injury information being based, at least in part, on the comparison between the generated inertial data set and the reference data.

Clause 25: The method of clause 24, wherein the one or more actions comprise actions for one or more of a musculoskeletal assessment, a biomechanical assessment, a physiological assessment, a neuromuscular assessment, and a performance assessment.

Clause 26: The method of clause 24 or clause 25, wherein the predictive injury information comprises an indication of whether the individual has a low risk of injury, moderate risk of injury, or high risk of injury.

Clause 27: The method of any of clauses 24 to 26, wherein the inertial measurement unit comprises three orthogonally positioned accelerometers for measuring acceleration along the x, y, and z axes.

Clause 28: The method of clause 27, wherein the inertial measurement unit further comprises three gyroscopes oriented along the x, y, and z axes respectively.

Clause 29: The method of any of clauses 24 to 28, further comprising transmitting the determined predictive injury information to art external computer network.

Clause 30: The method of any of clauses 24 to 29, wherein the reference data comprises one or more reference inertial data sets for the one or more physical actions.

Clause 31: A system for performing the method of any of clauses 24 to 30.

Clause 32: A computer implemented method for monitoring neuromuscular, physiological, biomechanical, or musculoskeletal activity of a subject based on information received from a wearable inertia measurement unit and adapted to be performed on a portable computing device, the method comprising: receiving and processing information from the inertial measurement unit representative of one or more physical actions performed by the subject; generating an inertial data set for the one or more physical action based on the received and processed information; comparing the generated inertial data set to reference data stored on computer readable memory in communication with the portable computing device; and causing an output component of the portable computing device to provide feedback comprising predictive injury information, the predictive injury information being based, at least in part, on the comparison between the generated inertial data set and the one or more reference data sets.

Clause 33: The computer implemented method of clause 32, wherein the reference data comprises one or more reference inertial data sets for the one or more physical actions performed by the subject.

What is claimed is:

1. A neuromuscular, physiological, biomechanical, or musculoskeletal activity monitoring system for a subject, the system comprising:
a wearable inertial measurement unit comprising at least one accelerometer and/or at least one gyroscope, the inertial measurement unit being configured to be worn by the subject and to obtain first and second kinematic data, the first and second kinematic data comprising one or more of angle of movement, movement velocity, acceleration, and/or impact force; and a controller in communication with an output component, the controller configured to:

receive and process the first kinematic data from the inertial measurement unit representative of one or more physical actions performed by the subject;

generate an inertial data set for the one or more physical actions based on the received and processed first kinematic data;

compare values of the generated inertial data set to threshold values for a subject;

remove values of the generated inertial data set from the generated inertial data set that exceed the threshold values for a subject;

provide a notification via the output component if the threshold values for a subject are exceeded to re-perform the one or more physical actions;

compare the generated inertial data set to reference data stored on computer readable memory in communication with the controller; and update the reference data with the generated inertial data set;

cause the output component to provide feedback comprising predictive injury information and a recommended training regimen configured to reduce a risk of injury, the predictive injury information and the recommended training regimen selected based at least in part on the comparison between the generated data set and the reference data;

receive and process the second kinematic data from the inertial measurement unit representative of one or more physical actions performed by the subject;

generate a second inertial data set for the one or more physical action based on the received and processed second kinematic data;

compare the second inertial data set to the updated reference data; and determine, based on the comparison, efficacy of the recommended training regimen in reducing the risk of injury.

2. The system of claim 1, wherein the one or more actions comprise actions for one or more of a musculoskeletal assessment, a biomechanical assessment, a physiological assessment, a neuromuscular assessment, and a performance assessment.

3. The system of claim 1, wherein the predictive injury information comprises an indication of whether the individual has an injury risk selected from the group consisting of a low risk of injury, a moderate risk of injury, or a high risk of injury.

4. The system of claim 1, wherein the reference data comprises one or more reference inertial data sets for the one or more physical actions performed by the subject.

5. The system of claim 1, wherein comparing the generated inertial data set to the reference data comprises determining a deviation between at least a portion of the generated inertial data set and the reference data, and wherein the predictive injury information is based on a magnitude of the deviation.

6. The system of claim 1, wherein the recommended training regimen comprises one or more of stretching, strength building actions, and aerobic or anaerobic exercises.

7. The system of claim 1, wherein the controller is associated with an intermediary device, the intermediary device comprising:

a first wireless transceiver for receiving the kinematic data from the inertial measurement unit;

a second wireless transceiver for transmitting processed kinematic data to an external computer network; and a visual display for providing feedback to the user.

8. The system of claim 1, wherein the inertial measurement unit comprises three orthogonally positioned accelerometers for measuring acceleration along the x, y, and z axes and three gyroscopes oriented along the x, y, and z axes respectively.

9. The system of claim 1, further comprising an input component in communication with the controller, wherein the controller is configured to receive subject demographic information about the subject entered via the input component, wherein the subject demographic information comprises one or more of subject height, weight, body mass index, occupation, activity level, and injury history.

10. The system of claim 9, wherein the feedback comprising predictive injury information is based, at least in part, on the received subject demographic information.

11. The system of claim 1, wherein the controller is configured to cause the output component to provide instructions to a user for placing the inertial measurement unit on the subject and for performing the one or more physical actions, and wherein the kinematic data from the inertial measurement unit is collected as the one or more physical actions are being performed.

12. A method of monitoring neuromuscular, physiological, biomechanical, or musculoskeletal activity of a subject, the method comprising:

placing an inertial measurement unit comprising at least one accelerometer and/or at least one gyroscope on the subject;

obtaining first kinematic data representative of one or more inertial data sets from the inertial measurement unit during one or more physical actions performed by the subject, the first kinematic data comprising one or more of angle of movement, movement velocity, acceleration, and/or impact force;

generating a first inertial data set for the one or more physical actions based on the obtained first kinematic data;

comparing values of the generated first inertial data set to threshold values for a subject;

removing values of the generated first inertial data set from the generated first inertial data set that exceed the threshold values for a subject;

providing a notification via the output component if the threshold values for a subject are exceeded to re-perform the one or more physical actions;

comparing the generated first inertial data set to reference data for the one or more physical actions;

determining predictive injury information for the one or more physical actions performed by the subject, the predictive injury information being based, at least in part, on the comparison between the generated first inertial data set and the reference data;

updating the reference data with the generated first inertial data set;

providing feedback comprising the predictive injury information and a recommended training regimen configured to reduce a risk of injury for the subject, the predictive injury information and the recommended training regimen selected based, at least in part, on the comparison between the generated first inertial data set and the reference data, the recommended training regimen comprising one or more of stretching, strength building actions, and aerobic or anaerobic exercises;

obtaining second kinematic data from the inertial measurement unit during one or more physical actions performed by the subject, the second kinematic data comprising one or more of angle of movement, movement velocity, acceleration, and/or impact force;

receiving and processing the second kinematic data from the inertial measurement unit representative of one or more physical actions performed by the subject;

generating a second inertial data set for the one or more physical actions based on the received and processed second kinematic data;

comparing the second inertial data set to the updated reference data; and determining, based on the comparison, efficacy of the recommended training regimen in reducing the risk of injury.

13. The method of claim 12, wherein the one or more actions comprise actions for one or more of a musculoskeletal assessment, a biomechanical assessment, a physiological assessment, a neuromuscular assessment, and a performance assessment.

14. A computer implemented method for monitoring neuromuscular, physiological, biomechanical, or musculoskeletal activity of a subject based on information received from a wearable inertia measurement unit adapted to be performed on a portable computing device, the method comprising:

receiving and processing first kinematic data from the inertial measurement unit representative of one or more physical actions performed by the subject, the first kinematic data comprising one or more of angle of movement, movement velocity, acceleration, and/or impact force;

generating an inertial data set for the one or more physical action based on the received and processed first kinematic data;

comparing values of the generated inertial data set to threshold values for a subject;

removing values of the generated inertial data set from the generated inertial data set that exceed the threshold values for a subject;

providing a notification via the output component if the threshold values for a subject are exceeded to re-perform the one or more physical actions;

comparing the generated inertial data set to reference data stored on computer readable memory in communication with the portable computing device;

updating the reference data with the generated inertial data set;

causing an output component of the portable computing device to provide feedback comprising predictive injury information and a recommended training regimen configured to reduce a risk of injury for the subject, the recommended training regimen selected based, at least in part, on the comparison between the generated data set and the reference data, the predictive injury information being based, at least in part, on the comparison between the generated inertial data set and the reference data;

receiving and processing second kinematic data from the inertial measurement unit representative of one or more physical actions performed by the subject;

generating a second inertial data set for the one or more physical action based on the received and processed second kinematic data;

comparing the second inertial data set to the updated reference data stored on computer readable memory in communication with the portable computing device; and determining, based on the comparison, efficacy of the recommended training regimen in reducing the risk of injury.

* * * * *

UNITED STATES PATENT AND TRADEMARK OFFICE
CERTIFICATE OF CORRECTION

| | |
|---|---|
| PATENT NO. | : 11,389,083 B2 |
| APPLICATION NO. | : 15/766165 |
| DATED | : July 19, 2022 |
| INVENTOR(S) | : Heather Bansbach et al. |

It is certified that error appears in the above-identified patent and that said Letters Patent is hereby corrected as shown below:

In the Specification

Column 1, Line 10, Delete "international" and insert -- International --

In the Claims

Column 29, Line 25, Claim 14, Delete "inertia" and insert -- inertial --

Signed and Sealed this
Eighteenth Day of October, 2022

*Katherine Kelly Vidal*

Katherine Kelly Vidal
*Director of the United States Patent and Trademark Office*